United States Patent

Amii et al.

(10) Patent No.: US 10,450,253 B2
(45) Date of Patent: Oct. 22, 2019

(54) PREPARATION PROCESS OF PERFLUOROALKYL COMPOUND WITH MONOHYDROPERFLUOROALKANE AS STARTING MATERIAL

(71) Applicants: KANTO DENKA KOGYO CO., LTD., Tokyo (JP); NATIONAL UNIVERSITY CORPORATION GUNMA UNIVERSITY, Maebashi-shi, Gunma (JP)

(72) Inventors: Hideki Amii, Maebashi (JP); Kazuki Komoda, Maebashi (JP); Masafumi Kobayashi, Tokyo (JP); Yutaka Nakamura, Kurashiki (JP); Ryusuke Obinata, Kurashiki (JP); Akinori Harada, Kurashiki (JP)

(73) Assignees: KANTO DENKA KOGYO CO., LTD., Tokyo (JP); NATIONAL UNIVERSITY CORPORATION GUNMA UNIVERSITY, Gunma (JP)

( * ) Notice: Subject to any disclaimer, the term of this patent is extended or adjusted under 35 U.S.C. 154(b) by 0 days.

(21) Appl. No.: 16/323,299

(22) PCT Filed: Feb. 16, 2017

(86) PCT No.: PCT/JP2017/005726
§ 371 (c)(1),
(2) Date: Feb. 5, 2019

(87) PCT Pub. No.: WO2018/025429
PCT Pub. Date: Feb. 8, 2018

(65) Prior Publication Data
US 2019/0169107 A1 Jun. 6, 2019

(30) Foreign Application Priority Data
Aug. 5, 2016 (JP) .................. 2016-154640

(51) Int. Cl.
C07C 29/38 (2006.01)
C07C 31/125 (2006.01)
C07C 33/46 (2006.01)
C07C 35/48 (2006.01)
C07C 43/23 (2006.01)
C07C 209/68 (2006.01)
C07C 211/48 (2006.01)
C07C 231/12 (2006.01)
C07C 233/15 (2006.01)
C07C 41/30 (2006.01)
C07C 209/78 (2006.01)

(52) U.S. Cl.
CPC ............ C07C 29/38 (2013.01); C07C 31/125 (2013.01); C07C 33/46 (2013.01); C07C 35/48 (2013.01); C07C 41/30 (2013.01); C07C 43/23 (2013.01); C07C 209/68 (2013.01); C07C 209/78 (2013.01); C07C 211/48 (2013.01); C07C 231/12 (2013.01); C07C 233/15 (2013.01)

(58) Field of Classification Search
CPC ....... C07C 29/38; C07C 29/62; C07C 313/04; C07C 319/14; C07C 33/46; C07C 323/03
See application file for complete search history.

(56) References Cited

U.S. PATENT DOCUMENTS

| 4,484,993 | A | 11/1984 | Ishikawa et al. |
| 6,096,926 | A | 8/2000 | Roques et al. |
| 6,203,721 | B1 | 3/2001 | Roques et al. |
| 6,355,849 | B1 | 3/2002 | Roques et al. |
| 2003/0065135 | A1 | 4/2003 | Schneider et al. |
| 2004/0230079 | A1* | 11/2004 | Prakash ................. C07C 29/38 568/56 |
| 2014/0006640 | A1 | 1/2014 | Subramanian |
| 2014/0039182 | A1* | 2/2014 | Colby .................... C07C 29/38 540/579 |

FOREIGN PATENT DOCUMENTS

| JP | 51075013 | A | 6/1976 |
| JP | 54098707 | A | 3/1981 |
| JP | 58065233 | A | 10/1984 |
| JP | 2000500480 | A | 1/2000 |
| JP | 2001506593 | A | 5/2001 |
| JP | 2003055385 | A | 2/2003 |

(Continued)

OTHER PUBLICATIONS

Prakash, et al., "Fluoride-Induced Trifluoromethylation of Carbonyl Compounds with Trifluromethyltrimthylsilane (TMS-CF3)" J. Am. Chem. Soc., pp. 393-395, vol. 111 (1989).
Prakash, et al., "Perfluoroalkylation with Organosilicon Reagents" Chem. Rev., pp. 757-786, vol. 97 (Jan. 1997).
Singh et al., "Nucleophilic Trifluoromethylation Reactions of Organic Compounds with (Trifluoromethyl)trimethylsilane" Tetrahedron, pp. 7613-7632, vol. 56 (Jun. 2000).
Kawai et al.,"Synthesis of novel C2-symmetric chiral crown ethers and their application to enantioselective trifluoromethylation of aldehydes and ketones", J. Fluorine Chem., pp. 762-765, vol. 130 (Jun. 2009).

(Continued)

*Primary Examiner* — Jafar F Parsa
(74) *Attorney, Agent, or Firm* — Browdy and Neimark, PLLC

(57) ABSTRACT

A simple production process is provided of a perfluoroalkyl compound that uses monohydroperfluoroalkane as a starting material, the perfluoroalkyl compound being an important intermediate of organic electronic materials, medicine, agricultural chemicals, functional polymer materials and the like. With monohydroperfluoroalkane is reacted a base and then a carbonyl compound to produce an alcohol having a perfluoroalkyl group. For example, potassium hydroxide is made to interact with trifluoromethane, and a reaction with a carbonyl compound is induced to produce an alcohol having a trifluoromethyl group.

12 Claims, No Drawings

(56) References Cited

FOREIGN PATENT DOCUMENTS

| JP | 2014091691 A | 5/2014 |
|---|---|---|
| JP | 2014519486 A | 8/2014 |
| WO | 9822435 A1 | 5/1998 |

OTHER PUBLICATIONS

Singh et al., "Cesium Fluoride Catalyzed Trifluoromethylation of Esters, Aldehydes, and Ketones with Triifluoromethyl) trimethylsilane", J. Org. Chem., pp. 2873-2876, vol. 64 (Mar. 1999).
Kolomeitsev et al., "A Convenient Route to Aryl Trifluoromethyl Sulfones by Fluoride-CatalyzedCross-Coupling of Arenesulfonyl Fluorides with (Trifluoromethyl)trimethylsilane and(Trifluoromethyl)trimethylstannane", Synthesis, pp. 1151-1152 (Dec. 1990).
Surya Prakash et al., "Taming of Fluoroform: Direct Nucleophilic Trifluoromethylation of Si, B, S, and C Centers", Science, pp. 1324-1327, vol. 338 (Oct. 2012).
Folleas et al., "Fluoroform: an effcient precursor for the trifluoromethylation of aldehydes" Tetrahedron Lett., pp. 2973-2976, vol. 39 (Feb. 1998).
Large et al., "Nucleophilic Trifluoromethylation of Carbonyl Compounds and Disulfides with Trifluoromethane and Silicon-Containing Bases" J. Org. Chem., pp. 8848-8856, vol. 65 (Oct. 2000).
Folleas et al.,"Fluoroform: an Efficient Precursor for the Triftuoromcthylation of Aldehydes", Tetrahedron, pp. 275-283 vol. 56 (Jun. 1999).
Shono, et al., "Electroorganic Chemistry. 130.1 A Novel Trifiuoromethylation of Aldehydes and Ketones Promoted by an Electrogenerated Bas", J. Org. Chem., pp. 2-4, vol. 56 (Oct. 1990).
Barhdadi, et al., "Coupling of fluoroform with aldehydes using an electrogenerated base", J. Chem. Soc., Chem. Commun. pp. 1251-1252 (Jan. 1998).
Zhang, et al., "Organocatalysis approach to trifluoromethylation with fluoroform", J. Fluorine Chem., pp. 367-371, vol. 156 (Jul. 2013).
Kawai et al., A sterically demanding organo-superbaseavoids decomposition of a naked trifluoromethyl carbanion directly generated from fluoroformtOrg. Biomol. Chem., pp. 1446-1450, vol. 11 (Jan. 2013).
Okusu et al., "Organocatalyzed Trifluoromethylation of Ketones and Sulfonyl Fluorides by Fluoroform under a Superbase System", ChemistryOpen, pp. 581-585, vol. 4 (2015).
Olmstead, et al., "Acidities of Water and Simple Alcohols in Dimethyl Sulfoxide Solution", J. Org. Chem, pp. 3295-3299, vol. 45 (Oct. 1979).
Russell et al., "Effective Nucleophilic Trifluoromethylation with Fluoroform and Common Base",Tetrahedron, (Sep. 1998), pp. 13771-13782, vol. 54.
International Search Report of PCT/JP2017/005726.

* cited by examiner

PREPARATION PROCESS OF PERFLUOROALKYL COMPOUND WITH MONOHYDROPERFLUOROALKANE AS STARTING MATERIAL

TECHNICAL FIELD

The present invention relates to a simple production process of a perfluoroalkyl compound that uses monohydroperfluoroalkane as a starting material, the perfluoroalkyl compound being an important intermediate of organic electronic materials, medicine, agricultural chemicals, functional polymer materials and the like.

BACKGROUND ART

Organic compounds having a perfluoroalkyl group are important intermediates of organic electronic materials, medicine, agricultural chemicals, functional polymer materials and the like. Many synthetic examples have been reported of trifluoromethyl compounds among others.

The Ruppert-Prakash reagent (trifluoromethyltrimethylsilane, $CF_3SiMe_3$) is known as a trifluoromethyl source used in the trifluoromethylation reaction of organic compounds, and it has been reported that a reaction with the following organic compounds provides a corresponding trifluoromethyl compound: aldehyde (Non-Patent Document 2, Non-Patent Document 3, Non-Patent Document 4, Non-Patent Document 5), ketone (Non-Patent Document 1, Non-Patent Document 2, Non-Patent Document 3, Non-Patent Document 4, Non-Patent Document 5), ester (Non-Patent Document 2, Non-Patent Document 3, Non-Patent Document 5), lactone (Non-Patent Document 2), acid halide (Non-Patent Document 2), amide (Non-Patent Document 2, Non-Patent Document 3), imide (Non-Patent Document 2), aziridine (Non-Patent Document 2), alkyl halide (Non-Patent Document 2), aryl halide (Non-Patent Document 2), sulfur compounds (Non-Patent Document 2), organic metal compounds (Non-Patent Document 2), nitroso compounds (Non-Patent Document 2), phosphorus compounds (Non-Patent Document 2, Non-Patent Document 3), imine (Non-Patent Document 3), porphyrin (Non-Patent Document 3), arylsulfonyl fluoride (Non-Patent Document 6), etc. It is however undeniable that the high cost of trifluoromethyltrimethylsilane presents a barrier to mass production.

Meanwhile, trifluoromethane is a material with a potential of being a trifluoromethyl source, since it is industrially mass produced as a byproduct in the Teflon (Registered Trademark) production process, so that it may be obtained in a large quantity at a low cost. There have been reported examples of Synthesizing trifluoromethyl compounds that correspond to the following materials by using trifluoromethane in a reaction with those materials: aldehyde (Non-Patent Document 7, Non-Patent Document 8, Non-Patent Document 10, Non-Patent Document 11, Non-Patent Document 12, Non-Patent Document 13, Non-Patent Document 14, Patent Document 3, Patent Document 4), ketone (Non-Patent Document 7, Non-Patent Document 9, Non-Patent Document 11, Non-Patent Document 13, Non-Patent Document 14, Non-Patent Document 15, Patent Document 1, Patent Document 2, Patent Document 4), ester (Non-Patent Document 7, Non-Patent Document 13, Patent Document 4), acid halide (Non-Patent Document 7, Non-Patent Document 13), boron compound (Non-Patent Document 7, Patent Document 4), silicon compound (Non-Patent Document 7, Patent Document 4), elemental sulfur (Non-Patent Document 7, Patent Document 4), disulfide (Non-Patent Document 14), epoxide (Non-Patent Document 13), carbon dioxide (Non-Patent Document 13, Patent Document 4), alkyl halide (Patent Document 4), aryl halide (Patent Document 4), arylsulfonyl fluoride (Non-Patent Document 15), etc. However, trifluoromethane has a low boiling point (−83° C.) and a low reactivity due to low acidity (pKa=27), so the activation of trifluoromethane requires a strong base, such as a base generated by an electrochemical method (Non-Patent Document 11, Non-Patent Document 12), phosphazene base (Non-Patent Document 13, Non-Patent Document 14, Non-Patent Document 15, Patent Document 3), potassium tert-butoxide (Non-Patent Document 9), potassium hexamethyl disilazide (Non-Patent Document 8, Non-Patent Document 9, Patent Document 1, Patent Document 2, Patent Document 4), sodium hydride (Non-Patent Document 9), potassium dimsylate (Non-Patent Document 8, Non-Patent Document 10). These strong bases are costly, and at the present stage, they are not necessarily good for application to industrial mass production. There is also a report that reaction proceeds by using a catalytic amount of base (Non-Patent Document 15), but the substrate is limited, and the method is not generally applicable.

Meanwhile, no synthetic example other than trifluoromethane which uses $R_FH$ (monohydroperfluoroalkane) represented by General Formula [3] has been reported so far.

BACKGROUND ART DOCUMENTS

Non-Patent Documents

[Non-Patent Document 1] *J. Am. Chem. Soc.*, 1989, 111, p 393-395
[Non-Patent Document 2] *Chem. Rev.*, 1997, 97, p 757-786
[Non-Patent Document 3] *Tetrahedron*, 2000, 56, p 7613-7632
[Non-Patent Document 4] *J. Fluorine Chem.*, 2009, 130, p 762-765
[Non-Patent Document 5] *J. Org. Chem.*, 1999, 64, p 2873-2876
[Non-Patent Document 6] *Synthesis*, 1990, p 1151-1152
[Non-Patent Document 7] *Science*, 2012, 338, p 1324-1327
[Non-Patent Document 8] *Tetrahedron Lett.*, 1998, 39, p 2973-2976
[Non-Patent Document 9] *J. Org. Chem.*, 2000, 65, p 8848-8856
[Non-Patent Document 10] *Tetrahedron*, 2000, 56, p 275-283
[Non-Patent Document 11] *J. Org. Chem.*, 1991, 56, p 2-4
[Non-Patent Document 12] *J. Chem. Soc., Chem. Commun.*, 1998, p 1251-1252
[Non-Patent Document 13] *J. Fluorine Chem.*, 2013, 156, p 367-371
[Non-Patent Document 14] *Org. Biomol. Chem.*, 2013, 11, p 1446-1450
[Non-Patent Document 15] *ChemistryOpen*, 2015, 4, p 581-585
[Non-Patent Document 16] *J. Org. Chem.* 1980, 45, p 3295-3299

Patent Document

[Patent Document 1] WO 98/22435
[Patent Document 2] U.S. Pat. No. 6,355,849 B
[Patent Document 3] JP 2014-91691 A
[Patent Document 4] JP 2014-519486 A

SUMMARY OF INVENTION

Problem to be Solved by Invention

The object of the present invention is to provide a simple production process of a perfluoroalkyl compound that uses monohydroperfluoroalkane as a starting material, the perfluoroalkyl compound being an important intermediate of organic electronic materials, medicine, agricultural chemicals, functional polymer materials and the like.

The present inventors studied extensively with an object of using trifluoromethane, which is economical and obtainable in a large quantity, as a trifluoromethyl source as well as a generally applicable, economical base, instead of the conventional costly base, to develop a method for activating trifluoromethane and to induce it to a trifluoromethyl compound, and found a method of activating trifluoromethane by using potassium hydroxide as a generally applicable, economical base. The inventors were also successful in producing a trifluoromethyl compound with high selectivity and high yield by reacting trifluoromethane with a carbonyl compound. The present inventors also found that the method can be applied not just to the aforementioned trifluoromethane but also to pentafluoroethane, and also to $R_FH$ (monohydroperfluoroalkane) represented by General Formula [3], and thus completed the present invention.

Solution to Problem

The present invention provides the following aspects.

(1)

A production process of alcohol having a perfluoroalkyl group represented by General Formula [4]:

[Chem. 2]

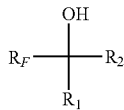

[4]

wherein, $R_F$ is a perfluoroalkyl group which is an alkyl group that may have a straight chain of 1 to 2 carbons, or a straight chain, branched chain or ring structure of 3 to 10 carbons, and which has all hydrogens on carbon substituted with fluorine; and $R^1$ and $R^2$ are each independently a hydrogen atom or an alkyl group, aryl group, heteroaryl group, aralkyl group, alkenyl group, or alkynyl group that may have a straight chain of 1 to 2 carbons, or a straight chain, branched chain or ring structure of 3 to 10 carbons, and that may have a substituent; and $R^1$ and $R^2$ may be merged to form a ring; the production process comprising: reacting in an organic solvent a carbonyl compound represented by General Formula [1]:

[Chem. 1]

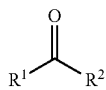

[1]

wherein, $R^1$ and $R^2$ are each independently a hydrogen atom or an alkyl group, aryl group, heteroaryl group, aralkyl group, alkenyl group, or alkynyl group that may have a straight chain of 1 to 2 carbons, or a straight chain, branched chain or ring structure of 3 to 10 carbons, and that may have a substituent; and $R^1$ and $R^2$ may be merged to form a ring;

a hydroxide represented by General Formula [2]:

$$M(OH)_x \qquad [2]$$

wherein, M is a metal belonging to Group I, Group II, Group III, Group IV, Group V, Group VI, Group VII, Group VIII, Group IX, Group X, Group XI, Group XII, and Group XIII in a periodic table of elements or ammonium that may be unsubstituted or that may have an alkyl group of 1 to 10 carbons as a substituent, which may be used alone or in a mixture of multiple substances, and x is equal to an oxidation number of a substance represented by M; and monohydroperfluoroalkane represented by General Formula [3]:

$$R_FH \qquad [3]$$

wherein, $R_F$ is a perfluoroalkyl group which is an alkyl group that may have a straight chain of 1 to 2 carbons, or a straight chain, branched chain or ring structure of 3 to 10 carbons, and which has all hydrogens on carbon substituted with fluorine.

(2)

The process according to (1), wherein $R_FH$ represented by General Formula [3] is trifluoromethane.

(3)

The process according to (1), wherein $R_FH$ represented by General Formula [3] is pentafluoroethane.

(4)

The process according to (1), wherein $M(OH)_x$ represented by General Formula [2] is potassium hydroxide.

(5)

The process according to (1), wherein $M(OH)_x$ represented by General Formula [2] is sodium hydroxide.

(6)

The process according to (1), wherein $M(OH)_x$ represented by General Formula [2] is tetramethylammonium or a hydrate thereof.

(7) The process according to any one of (1) to (6), wherein $M(OH)_x$ represented by General Formula [2] is added to a reaction system as a powder.

(8)

The process according to any one of (1) to (7), wherein the organic solvent is dimethyl sulfoxide, dimethyl formamide, N-methylpyrrolidone, tetrahydrofuran, diglyme, acetonitrile, or a combination thereof.

(9)

The process according to any one of (1) to (8), wherein monohydroperfluoroalkane is in a gas state when it comes in contact with a reaction solution.

(10)

The process according to any one of (1) to (8) wherein monohydroperfluoroalkane is in a liquid or solid state when it is mixed with a reaction solution.

Advantageous Effects of Invention

The present invention made it possible to provide a simple production process of a perfluoroalkyl compound that uses monohydroperfluoroalkane, exemplified by trifluoromethane and pentafluoroethane, as a starting material, the perfluoroalkyl compound being an important intermediate of organic electronic materials, medicine, agricultural chemicals, functional polymer materials and the like. Among the aforementioned monohydroperfluoroalkanes, trifluoromethane is a gas with an especially high production amount and global warming effect, so its processing method and disposal method are addressed as problems. The present invention can provide an effective utilization method as well as processing method of trifluoromethane, having a high global warming effect, and thus, contribute materially from an economic and environmental perspective.

DESCRIPTION OF EMBODIMENTS

The present invention is described in detail below. The present invention provides a simple production process of a perfluoroalkyl compound using especially trifluoromethane, which is an industrially mass produced compound, as a starting material among the monohydroperfluoroalkanes represented by General Formula [4], and reacting it with a carbonyl compound represented by General Formula [1] under the presence of a hydroxide represented by General Formula [2], the perfluoroalkyl compound being an important intermediate of organic electronic materials, medicine, agricultural chemicals, functional polymer materials and the like.

The scope of the present invention is not limited by these descriptions, and the invention may be implemented by making appropriate corrections even if it is not described below, as long as they do not diverge from the objective of the present invention.

[Action]

The process of the present invention was found by experiments, and the study by the present inventors so far indicates that the hydroxide represented by General Formula [2] removes a hydrogen atom (proton) from monohydroperfluoroalkane represented by General Formula [3], and the resulting perfluoroalkyl anion attacks the carbon on the carbonyl group of the carbonyl compound represented by General Formula [1] to change the carbonyl group to a hydroxide group and to form a perfluoroalkyl alcohol represented by General Formula [4]. It was regarded in the conventional art that a special strong base was required in the step of removing a hydrogen atom (proton) from monohydroperfluoroalkane, so it was a surprise that the process of the present invention can be carried out by using a hydroxide represented by General Formula [2].

The trifluoromethyl anion is a far stronger base than a hydroxide ion because the pKa in water of trifluoromethane and water are respectively 32 and 15.7. Accordingly, the hydroxide ion does not normally cause hydrogen abstraction from trifluoromethane in water. However, the pKa of water changes substantially to 31.4 in DMSO (Non-Patent Document 16). Although an accurate comparison cannot be made since there is no report of a pKa value of trifluoromethane in DMSO, the pKa of trifluoromethane and water is in a close vicinity in DMSO, so it is presumed that the hydrogen abstraction from trifluoromethane by the hydroxide ion proceeds in DMSO. Likewise, reactions are considered to proceed by the present reaction mechanism in solvents other than DMSO used in the present invention.

[Carbonyl Compound Represented by General Formula [1]]

The carbonyl compound represented by General Formula [1] of the present invention is not particularly limited, and the substituents represented by $R^1$, $R^2$ are each a hydrogen atom or an alkyl group, aryl group, heteroaryl group, aralkyl group, alkenyl group or alkynyl group, that may have a straight chain with 1 to 2 carbons or a straight chain, branched chain or ring structure with 3 to 26 carbons, particularly 3 to 10 carbons, specifically, a methyl group, ethyl group, propyl group, isopropyl group, butyl group, isobutyl group, tert-butyl group, pentyl group, hexyl group, heptyl group, octyl group, nonyl group, decyl group, cyclopropyl group, cyclobutyl group, cyclopentyl group, cyclohexyl group, cycloheptyl group, cyclooctyl group, cyclononyl group, cyclodecyl group, phenyl group, naphthyl group, anthranyl group, naphthacenyl group, pentacenyl group, hexacenyl group, coronyl group, pyrrolyl group, furyl group, thienyl group, pyridyl group, pyrimidyl group, pyrazyl group, pyridazyl group, pyrazolyl group, imidazolyl group, oxazolyl group, thiazolyl group, indolyl group, benzofuryl group, benzothienyl group, quinolyl group, isoquinolyl group, quinoxalyl group, phthalazyl group, quinazolyl group, naphthyridyl group, cinnolyl group, benzimidazolyl group, benzoxazolyl group, benzothiazolyl group, benzyl group, phenethyl group, vinyl group, allyl group, prenyl group, propagyl group; the carbon atoms thereof may be substituted with atoms other than the hydrogen atom, such as nitrogen, oxygen, silicon, phosphorus, sulfur, fluorine, chlorine, bromine, iodine, etc., or with substituents other than the hydrogen atom, including an alkyl group, aryl group, heteroaryl group, aralkyl group, alkenyl group, alkynyl group, hydroxy group, hydroperoxy group, dioxy group, carboxyl group, thiocarboxy group, dithiocarboxy group, carbonyl group, thiocarbonyl group, oxycarbonyl group, haloformyl group, carbamoyl group, an alkoxy group such as methoxy group, ethoxy group, an amino group such as dimethylamino group, acetamino group (AcHN—), imino group, hydrazino group, a halogen-substituted alkyl group such as trifluoromethyl group, difluoromethyl group, trichloromethyl, sulfanyl group, alkylsulfinyl group, alkylsulfonyl group, sulfo group, sulfino group, cyano group, isocyano group, cyanato group, isocyanato group, thiocyanato group, isothiocyanato group, nitro group, nitroso group, diazo group, azide group, amidino group, formyl group, thioformyl group. Specific examples include benzophenone, acetophenone, undecan-2-one, 4'-methoxyacetophenone, 3'-methoxyacetophenone, 2'-methoxyacetophenone, 4'-dimethylaminoacetophenone, 4'-acetamideacetophenone, 4'-fluoroacetophenone, 4'-chloroacetophenone, 3'-bromoacetophenone, pivalaldehyde, benzaldehyde, acetaldehyde, formaldehyde.

Additionally, $R^1$ and $R^2$ may be merged to form an aliphatic ring or a heterocyclic ring having 3 to 26 carbons, particularly 3 to 10 carbons; specific examples include cyclopropanone, cyclobutanone, cyclopentanone, cyclohexanone, cycloheptanone, cyclooctanone, cyclononanone, cyclodecanone, 3-pyrrolidinone, N-methyl-3-pyrrolidinone, N-ethyl-3-pyrrolidinone, N-propyl-3-pyrrolidinone, N-isopropyl-3-pyrrolidinone, N-butyl-3-pyrrolidinone, N-isobutyl-3-pyrrolidinone, N-tert-butyl-3-pyrrolidinone, N-pentyl-3-pyrrolidinone, N-hexyl-3-pyrrolidinone, N-heptyl-3-pyrrolidinone, N-octyl-3-pyrrolidinone, N-nonyl-3-pyrrolidinone, N-decyl-3-pyrrolidinone, N-cyclopropyl-3-pyrrolidinone, N-cyclobutyl-3-pyrrolidinone, N-cyclopentyl-3-pyrrolidinone, N-cyclohexyl-3-pyrrolidinone, N-cycloheptyl-3-pyrrolidinone, N-cyclooctyl-3-pyrrolidinone, N-cyclononyl-3-pyrrolidinone, N-cyclodecyl-3-pyrrolidinone, N-phenyl-3-pyrrolidinone, N-naphthyl-3-pyrrolidinone, N-anthranyl-3-pyrrolidinone, N-naphthacenyl-3-pyrrolidinone, N-pentacenyl-3-pyrrolidinone, N-hexacenyl-3-pyrrolidinone, N-coronyl-3-pyrrolidinone, N-pyrrolyl-3-pyrrolidinone, N-furyl-3-pyrrolidinone, N-thienyl-3-pyrrolidinone, N-pyridyl-3-pyrrolidinone, N-pyrimidyl-3-pyrrolidinone, N-pyrazyl-3-pyrrolidinone, N-pyridazyl-3-pyrrolidinone, N-pyrazolyl-3-pyrrolidinone, N-imidazolyl-3-pyrrolidinone, N-oxazolyl-3-pyrrolidinone, N-thiazolyl-3-pyrrolidinone, N-indolyl-3-pyrrolidinone, N-benzofuryl-3-pyrrolidinone, N-benzothienyl-3-pyrrolidinone, N-quinolyl-3-pyrrolidinone, N-isoquinolyl-3-pyrrolidinone, N-quinoxalyl-3-pyrrolidinone, N-phthalazyl-3-pyrrolidinone, N-quinazolyl-3-pyrrolidinone, N-naphthyridyl-3-pyrrolidinone, N-cinnolyl-3-pyrrolidinone, N-benzimiidazolyl-3-pyrrolidinone, N-benzoxazolyl-3-pyrrolidinone, N-benzothiazolyl-3-pyrrolidinone, N-benzyl-3-pyrrolidinone, N-phenethyl-3-pyrrolidinonc, N-vinyl-3-pyrrolidinonc, N-allyl-3-pyrrolidinone, N-prenyl-3-pyrrolidinone, N-propagyl-3-pyrrolidinone, 4,5-dihydro-3(2H)-furanone, 4,5-dihydro-3(2H)-thiophenone, 3-piperidinone, N-methyl-3-piperidinone, N-ethyl-3-piperidinone, N-propyl-3-piperidinone, N-isopropyl-3-piperidinone, N-butyl-3-piperidinone, N-isobutyl-3-piperidinone, N-tert-butyl-3-piperidinone, N-pentyl-3-piperidinone, N-hexyl-3-piperidinone, N-heptyl-3-piperidinone, N-octyl-3-piperidinone, N-nonyl-3-piperidinone, N-decyl-3-piperidinone, N-cyclopropyl-3-piperidinone, N-cyclobutyl-3-piperidinone, N-cyclopentyl-3-piperidinone, N-cyclohexyl-3-piperidinone, N-cycloheptyl-3-piperidinone, N-cyclooctyl-3-piperidinone, N-cyclononyl-3-piperidinone, N-cyclodexyl-3-piperidinone, N-phenyl-3-piperidinone, N-naphthyl-3-piperidinone, N-anthranyl-3-piperidinone, N-naphthacenyl-3-piperidinone, N-pentacenyl-3-piperidinone, N-hexacenyl-3-piperidinone, N-coronyl-3-piperidinone, N-pyrrolyl-3-piperidinone, N-furyl-3-piperidinone, N-thienyl-3-piperidinone, N-pyridyl-3-piperidinone, N-pyrimidyl-3-piperidinone, N-pyrazyl-3-piperidinone, N-pyridazyl-3-piperidinone, N-pyrazolyl-3-piperidinone, N-imidazolyl-3-piperidinone, N-oxazolyl-3-piperidinone, N-thiazolyl-3-piperidinone, N-indolyl-3-piperidinone, N-benzofuryl-3-piperidinone, N-benzothienyl-3-piperidinone, N-quinolyl-3-piperidinone, N-isoquinolyl-3-piperidinone, N-quinoxalyl-3-piperidinone, N-phthalazyl-3-piperidinone, N-quinazolyl-3-piperidinone, N-naphthyridyl-3-piperidinone, N-cinnolyl-3-piperidinone, N-benzimidazolyl-3-piperidinone, N-benzoxazolyl-3-piperidinone, N-benzothiazolyl-3-piperidinone, N-vinyl-3-piperidinone, N-allyl-3-piperidinone, N-prenyl-3-piperidinone, N-propagyl-3-piperidinone, dihydro-2H-pyran-3(4H)-one, dihydro-2H-thiopyran-3(4H)-one, 4-piperidinone, N-methyl-4-piperidinone, N-ethyl-4-piperidinone, N-propyl-4-piperidinone, N-isopropyl-4-piperidinone, N-butyl-4-piperidinone, N-isobutyl-4-piperidinone, N-text-butyl-4-piperidinone, N-pentyl-4-piperidinone, N-hexyl-4-piperidinone, N-heptyl-4-piperidinone, N-octyl-4-piperidinone, N-nonyl-4-piperidinone, N-decyl-4-piperidinone, N-cyclopropyl-4-piperidinone, N-cyclobutyl-4-piperidinone, N-cyclopentyl-4-piperidinone, N-cyclohexyl-4-piperidinone, N-cycloheptyl-4-piperidinone, N-cyclooctyl-4-piperidinone, N-cyclononyl-4-piperidinone, N-cyclodecyl-4-piperidinone, N-phenyl-4-piperidinone, N-naphthyl-4-piperidinone, N-anthranyl-4-piperidinone, N-naphthacenyl-4-piperidinone, N-pentacenyl-4-piperidinone, N-hexacenyl-4-piperidinone, N-coronyl-4-piperidinone, N-pyrrolyl-4-piperidinone, N-furyl-4-piperidinone, N-thienyl-4-piperidinone, N-pyridyl-4-piperidinone, N-pyrimidyl-4-piperidinone, N-pyrazyl-4-piperidinone, N-pyridazyl-4-piperidinone, N-pyrazolyl-4-piperidinone, N-imidazolyl-4-piperidinone, N-oxazolyl-4-piperidinone, N-thiazolyl-4-piperidinone, N-indolyl-4-piperidinone, N-benzofuryl-4-piperidinone, N-benzothienyl-4-piperidinone, N-quinolyl-4-piperidinone, N-isoquinolyl-4-piperidinone, N-quinoxalyl-4-piperidinone, N-phthalazyl-4-piperidinone, N-quinazolyl-4-piperidinone, N-naphthyridyl-4-piperidinone, N-cinnolyl-4-piperidinone, N-benzimidazolyl-4-piperidinone, N-benzoxazolyl-4-piperidinone, N-benzothiazolyl-4-piperidinone, N-benzyl-4-piperidinone, N-phenethyl-4-piperidinone, N-vinyl-4-piperidinone, N-allyl-4-piperidinone, N-prenyl-4-piperidinone, N-propagyl-4-piperidinone, tetrahydro-4H-pyran-4-one, tetrahydro-4H-thiopyran-4-one. The carbons constituting the aliphatic ring or heterocyclic ring may have a group comprising an atom other than a hydrogen atom, such as nitrogen, oxygen, silicon, phosphorus, sulfur, fluorine, chlorine, bromine, iodine, etc. as a substituent; specific examples include 4-aminocyclohexanone, 4-(methylamino)cyclohexanone, 4-(ethylamino)cyclohexanone, 4-(propylamino)cyclohexanone, 4-(isopropylamino)cyclohexanone, 4-(butylamino)cyclohexanone, 4-(isobutylamino)cyclohexanone, 4-(tert-butylamino)cyclohexanone, 4-(pentylamino)cyclohexanone, 4-(hexylamino)cyclohexanone, 4-(heptylamino)cyclohexanone, 4-(octylamino)cyclohexanone, 4-(nonylamino)cyclohexanone, 4-(decylamino)cyclohexanone, 4-(cyclopropylamino)cyclohexanone, 4-(cyclobutylamino)cyclohexanone, 4-(cyclopentylamino)cyclohexanone, 4-(cyclohexylamino)cyclohexanone, 4-(cycloheptylamino)cyclohexanone, 4-(cyclooctylamino)cyclohexanone, 4-(cyclononylamino)cyclohexanone, 4-(cyclodecylamino)cyclohexanone, 4-(phenylamino)cyclohexanone, 4-(naphthylamino)cyclohexanone, 4-(anthranylamino)cyclohexanone, 4-(naphthacenylamino)cyclohexanone, 4-(pentacenylamino)cyclohexanone, 4-(hexacenylamino)cyclohexanone, 4-(coronylamino)cyclohexanone, 4-(pyrrolylamino)cyclohexanone, 4-(furylamino)cyclohexanone, 4-(thienylamino)cyclohexanone, 4-(pyridylamino)cyclohexanone, 4-(pyrimidylamino)cyclohexanone, 4-(pyrazylamino)cyclohexanone, 4-(pyridazylamino)cyclohexanone, 4-(pyrazolylamino)cyclohexanone, 4-(imidazolylamino)cyclohexanone, 4-(oxazolylamino)cyclohexanone, 4-(thiazolylaminoamino)cyclohexanone, 4-(indolylamino)cyclohexanone, 4-(benzofurylamino)cyclohexanone, 4-(benzothienylamino)cyclohexanone, 4-(quinolylamino)cyclohexanone, 4-(isoquinolylamino)cyclohexanone, 4-(quinoxalylamino)cyclohexanone, 4-(phthalazylamino)cyclohexanone, 4-(quinazolylamino)cyclohexanone, 4-(naphthyridylamino)cyclohexanone, 4-(cinnolylamino)cyclohexanone, 4-(benzimidazolylamino)cyclohexanone, 4-(benzoxazolylamino)cyclohexanone, 4-(benzothiazolylamino)cyclohexanone, 4-(benzylamino)cyclohexanone, 4-(phenethylamino)cyclohexanone, 4-(vinylamino)cyclohexanone, 4-(allylamino)cyclohexanone, 4-(prenylamino)cyclohexanone, 4-(propagylamino)cyclohexanone, 4-(dimethylamino)cyclohexanone, 4-(diethylamino)cyclohexanone, 4-(dipropylamino)cyclohexanone, 4-(diisopropylamino)cyclohexanone, 4-(dibutylamino)cyclohexanone, 4-(diisobutylamino)cyclohexanone, 4-(tert-butylamino)cyclohexanone, 4-(dipentylamino)cyclohexanone, 4-(dihexylamino)cyclohexanone, 4-(diheptylamino)cyclohexanone, 4-(dioctylamino)cyclohexanone, 4-(dinonylamino)cyclohexanone, 4-(didecylamino)cyclohexanone, 4-(dicyclopropylamino)cyclohexanone, 4-(dicyclobutylamino)cyclohexanone, 4-(dicyclopentylamino)cyclohexanone, 4-(dicyclohexylamino)cyclohexanone, 4-(dicycloheptylamino)cyclohexanone, 4-(dicyclooctylamino)cyclohexanon, 4-(dicyclononylamino)cyclohexanone, 4-(cyclodecylamino)cyclohexanone, 4-(diphenylamino)cyclohexanone, 4-(dinaphthylamino)cyclohexanone, 4-(dianthranylamino)cyclohexanone, 4-(dinaphthacenylamino)cyclohexanone, 4-(dipentacenylamino)cyclohexanone, 4-(dihexacenylamino)cyclohexanone, 4-(dicoronylamino)cyclohexanone, 4-(dipyrrolylamino)cyclohexanone, 4-(difurylamino)cyclohexanone, 4-(dithienylamino)cyclohexanone, 4-(dipyridylamino)cyclohexanone, 4-(dipyrimidylamino)cyclohexanone, 4-(dipyrazylamino)cyclohexanone, 4-(dipyridazylamino)cyclohexanone, 4-(dipyrazolylamino)cyclohexanone, 4-(diimidazolylamino)cyclohexanone, 4-(dioxazolylamino)cyclohexanone, 4-(dithiazolylamino)cyclohexanone, 4-(diindolylamino)cyclohexanone, 4-(dibenzofurylamino)cyclohexanone, 4-(dibenzothienylamino)cyclohexanone, 4-(diquinolylamino)cyclohexanone, 4-(diisoquinolylamino)cyclohexanone, 4-(diquinoxalylamino)cyclohexanone, 4-(diphthalazylamino)cyclohexanone, 4-(diquinazolylamino)cyclohexanone, 4-(dinaphthyridylamino)cyclohexanone, 4-(dicinnolylamino)cyclohexanone, 4-(dibenzimidazolylamino)cyclohexanone, 4-(dibenzoxazolylamino)cyclohexanon, 4-(dibenzothiazolylamino)cyclohexanone, 4-(dibenzylamino)cyclohexanone, 4-(diphenethylamino)cyclohexanone, 4-(divinylamino)cyclohexanone, 4-(diallylamino)cyclohexanone, 4-(diprenylamino)cyclohexanone, 4-dipropagylamino)cyclohexanone, 4-hydroxycyclohexanone, 4-(methoxy)cyclohexanone, 4-(ethoxy)cyclohexanone, 4-(propoxy)cyclohexanone, 4-(isopropoxy)cyclohexanone, 4-(butoxy)cyclohexanone, 4-(isobutoxy)cyclohexanone, 4-(tert-butoxy)cyclohexanone, 4-(pentyloxy)cyclohexanone, 4-(hexyloxy)cyclohexanone, 4-(heptyloxy)cyclohexanone, 4-(octyloxy)cyclohexanone, 4-(nonyloxy)cyclohexanone, 4-(decyloxy)cyclohexanone, 4-(cyclopropoxy)cyclohexanone, 4-(cyclobutoxy)cyclohexanone, 4-(cyclopentyloxy)cyclohexanone, 4-(cyclohexyloxy)cyclohexanone, 4-(cycloheptyloxy)cyclohexanone, 4-(cyclooctyloxy)cyclohexanone, 4-(cyclononyloxy)cyclohexanone, 4-(cyclodecyloxy)cyclohexanone, 4-(phenoxy)cyclohexanone, 4-(naphthoxy)cyclohexanone, 4-(anthracenyloxy)cyclohexanone, 4-(naphthacenyloxy)cyclohexanone, 4-(pentacenyloxy)cyclohexanone, 4-(hexacenyloxy)cyclohexanone, 4-(coronyloxy)cyclohexanone, 4-(pyrrolyloxy)cyclohexanone, 4-(furyloxy)cyclohexanone, 4-(thienyloxy)cyclohexanone, 4-(pyridyloxy)cyclohexanone, 4-(pyrimidyloxy)cyclohexanone, 4-(pyrazyloxy)cyclohexanone, 4-(pyridazyloxy)cyclohexanone, 4-(pyrazolyloxy)cyclohexanone, 4-(imidazolyloxy)cyclohexanone, 4-(oxazolyloxy)cyclohexanone, 4-(thiazolyloxy)cyclohexanone, 4-(indolyloxy)cyclohexanone, 4-(benzofuryloxy)cyclohexanone, 4-(benzothienyloxy)cyclohexanone, 4-(quinolyloxy)cyclohexanone, 4-(isoquinolyloxy)cyclohexanone, 4-(quinoxalyloxy)cyclohexanone, 4-(phthalazyloxy)cyclohexanone, 4-(quinazolyloxy)cyclohexanone, 4-(naphthyridyloxy)cyclohexanone, 4-(cinnolyloxy)cyclohexanone, 4-(benzimidazolyloxy)cyclohexanone, 4-(benzoxazolyloxy)cyclohexanone, 4-(benzothiazolyloxy)cyclohexanone, 4-(benzyloxy)cyclohexanone, 4-(phenethyloxy)cyclohexanone, 4-(vinyloxy)cyclohexanone, 4-(allyloxy)cyclohexanone, 4-(prenyloxy)cyclohexanone, 4-(propagyloxy)cyclohexanone, 4-mercaptocyclohexanone, 4-(methylthio)cyclohexanone, 4-(ethylthio)cyclohexanone, 4-(propylthio)cyclohexanone, 4-(isopropylthio)cyclohexanone, 4-(butylthio)cyclohexanone, 4-(isobutylthio)cyclohexanone, 4-tert-butylthio)cyclohexanone, 4-(pentylthio)cyclohexanone, 4-(hexylthio)cyclohexanone, 4-(heptylthio)cyclohexanone, 4-(octylthio)cyclohexanone, 4-(nonylthio)cyclohexanone, 4-(decylthio)cyclohexanone, 4-(cyclopropylthio)cyclohexanone, 4-(cyclobutylthio)cyclohexanone, 4-(cyclopentylthio)cyclohexanone, 4-(cyclohexylthio)cyclohexanone, 4-(cycloheptylthio)cyclohexanone, 4-(cyclooctylthio)cyclohexanone, 4-(cyclononylthio)cyclohexanone, 4-(cyclodccylthio)cyclohexanone, 4-(phenylthio)cyclohexanone, 4-(naphthylthio)cyclohexanone, 4-(anthranylthio)cyclohexanone, 4-(naphthacenylthio)cyclohexanone, 4-(pentacenylthio)cyclohexanonae, 4-(hexacenylthio)cyclohexanone, 4-(coronylthio)cyclohexanone, 4-(pyrrolylthio)cyclohexanone, 4-(furylthio)cyclohexanone, 4-(thienylthio)cyclohexanone, 4-(pyridylthio)cyclohexanone, 4-(pyrimidylthio)cyclohexanone, 4-(pyrazylthio)cyclohexanone, 4-(pyridazylthio)cyclohexanone, 4-(pyrazolylthio)cyclohexanone, 4-(imidazolylthio)cyclohexanone, 4-(oxazolylthio)cyclohexanone, 4-(thiazolylthio)cyclohexanone, 4-(indolylthio)cyclohexanone, 4-(benzofurylthio)cyclohexanone, 4-(benzothienylthio)cyclohexanone, 4-(quinolylthio)cyclohexanone, 4-(isoquinolylthio)cyclohexanone, 4-(quinoxalylthio)cyclohexanone, 4-(phthalazylthio)cyclohexanone, 4-(quinazolylthio)cyclohexanone, 4-(naphthyridylthio)cyclohexanone, 4-(cinnolylthio)cyclohexanone, 4-(benzimidazolylthio)cyclohexanone, 4-(benzoxazolylthio)cyclohexanone, 4-(benzothiazolylthio)cyclohexanone, 4-(benzylthio)cyclohexanone, 4-(phenethylthio)cyclohexanone, 4-(vinylthio)cyclohexanone, 4-(allylthio)cyclohexanone, 4-(prenylthio)cyclohexanone, 4-(propagylthio)cyclohexanone, 4-fluorocyclohexanone, 4-chlorocyclohexanone, 4-bromocyclohexanone, 4-iodocyclohexanone.

[Hydroxides Represented by General Formula [2]]

The hydroxide represented by General Formula [2] in the present invention is not particularly limited, and the substance represented by M may be mainly a hydroxide of metal belonging to Group I, Group II, Group II, Group IV, Group V, Group VI, Group VII, Group VIII, Group LX, Group X, Group XI, Group XII, and Group XII or of ammonium that is unsubstituted or that may have an alkyl group of 1 to 10 carbons as a substituent; specific examples include lithium hydroxide, sodium hydroxide, potassium hydroxide, rubidium hydroxide, caesium hydroxide, beryllium hydroxide, magnesium hydroxide, calcium hydroxide, strontium hydroxide, barium hydroxide, iron oxyhydroxide, copper hydroxide, zinc hydroxide, aluminum hydroxide, ammonium hydroxide, tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraheptylammonium hydroxide, tetraoctylammonium hydroxide, tetranonylammonium hydroxide, tetradecylammonium hydroxide. The 4 alkyl groups on the nitrogen atom forming the ammonium salt may all be the same, or all different, or 1 to 4 alkyl groups may be substituted with hydrogen, and an anhydride or hydrates (monohydrate to icosahydrate) may be used. The hydroxide represented by General Formula [2] may preferably be a combination of a monovalent cation and one hydroxide ion, more preferably sodium hydroxide, potassium hydroxide, tetramethylammonium hydroxide or hydrates thereof (particularly, pentahydrate).

[Monohydroperfluoroalkane Represented by General Formula [3]]

Monohydroperfluoroalkane represented by General Formula [3] in the present invention is not particularly limited, and the substance represented by $R_F$ is a perfluoroalkyl group which is an alkyl group that may have a straight chain having 1 to 2 carbons, or a straight chain, branched chain or ring structure having 3 to 26 carbons, particularly 3 to 10 carbons, and in which all hydrogens on the carbons are substituted with fluorine; specific examples include a trifluoromethyl group, pentafluoroethyl group, heptafluoropropyl group, heptafluoroisopropyl group, pentafluorocyclopropyl group, nonafluorobutyl group, nonafluoroisobutyl group, nonafluoro tert-butyl group, heptafluorocyclobutyl group, undecafluoropentyl group, nonafluorocyclopentyl group, tridecafluorohexyl group, undecafluorocyclohexyl group, pentadecafluoroheptyl group, tridecafluorocycloheptyl group, heptadecafluorooctyl group, pentadecacyclooctyl group, nonadecafluorononyl group, heptadecafluorocyclononyl group, henicosafluorodecenyl group, nonadecafluorocyclodecenyl group. Since it is inexpensive and available in a large amount, the monohydroperfluoroalkane represented by General Formula [3] is preferably trifluoromethane, pentafluoroethane, and more preferably trifluoromethane.

[Perfluoroalkylalcohol Represented by General Formula [4]]

Perfluoroalkylalcohol represented by General Formula [4] in the present invention is a corresponding perfluoroalkylalcohol with respectively the same substituents $R^1$ and $R^2$ as the $R^1$ and $R^2$ of General Formula [1].

[Reaction Condition]

Next, the reaction method in the present invention will be described in detail.

The material of the reaction container used in the present invention may be glass, plastic such as polyethylene and polypropylene, fluorine resin such as Teflon (Registered Trademark) and PFA, and metal such as stainless steel, HASTELLOY, and Inconel, of which glass is preferable. The reaction temperature may be in the range of −40° C. to 200° C., preferably 0° C. to 60° C. The reaction time may be from 1 to 100 hours, and preferably 3 to 6 hours.

The amount of monohydroperfluoroalkane to be used is about 0.1 mol equivalent to about 100 mol equivalent, preferably 1 mol equivalent to 10 mol equivalent, against the carbonyl compound represented by General Formula [1] used in the present invention.

The reaction pressure for performing the reaction may be in the range of an atmospheric pressure or lower ($1.0 \times 10^{-7}$ MPa to 0.09 MPa), normal pressure (about 0.1 MPa), or a pressurized state (0.11 to 4.87 MPa), but a reaction using a glass reactor is performed at a pressure of preferably $1.0 \times 10^{-7}$ MPa to 0.11 MPa, more preferably 0.01 MPa to 0.11 MPa. Meanwhile, a reaction using a metal reactor such as an autoclave is performed at preferably $0.09 \times 10^{-7}$ MPa to 4.87 MPa, more preferably 0.2 MPa to 1 MPa.

An introduction process of monohydroperfluoroalkane is explained in the case in which trifluoromethane is monohydroperfluoroalkane, but other gaseous monohydroperfluoroalkanes at standard conditions may be used in reactions by applying the same method. The interior of the reactor may be decompressed before use in a reaction and then put under a trifluoromethane atmosphere by introducing trifluoromethane, or the interior of the reactor may be replaced with inert gas such as nitrogen, helium and argon before introducing trifluoromethane to form a mixed gas of inert gas and trifluoromethane for reaction. Introduction of trifluoromethane may be conducted by a method of directly introducing trifluoromethane from a steel bottle or cylinder equipped with a pressure reducing valve to the reactor through a pipe, or a method of introducing trifluoromethane to the reactor from a sample bag or a rubber balloon filled in advance with trifluoromethane. At a small scale, the method of introducing trifluoromethane to the reactor from a rubber balloon is preferable, but at an industrial level, it is more preferable to introduce trifluoromethane into the reactor using a pipe. The method for contacting trifluoromethane and the reaction solution includes a method of contact/mixing at the gas-liquid interface or a method of mixing trifluoromethane with the reaction solution by liquefying trifluoromethane using a condenser, of which the method for contact/mixing at the gas-liquid interface is preferable.

Monohydroperfluoroalkane, which is liquid or solid at room temperature, may be used in a reaction by the same introduction method as a normal liquid material or solid material.

The carbonyl compound represented by General Formula [1] may have impurities removed by being subjected to a purification operation such as distillation before it is used in a reaction, but impurities that are included at an industrially available level are not a particular problem in carrying out the present production process, and the compound may be used without additional treatment.

In the hydroxide represented by General Formula [2], the substance represented by M may be mainly a hydroxide of metal belonging to Group I, Group II, Group III, Group IV, Group V, Group VI, Group VII, Group VIII, Group IX, Group X, Group XI, Group XII, and Group XIII or of ammonium that may be substituted; specific examples include lithium hydroxide, sodium hydroxide, potassium hydroxide, rubidium hydroxide, caesium hydroxide, beryllium hydroxide, magnesium hydroxide, calcium hydroxide, strontium hydroxide, and barium hydroxide, iron oxyhydroxide (III), copper hydroxide (I), copper hydroxide (II), zinc hydroxide, aluminum hydroxide, ammonium hydroxide, tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraheptylammonium hydroxide, tetraoctylammonium hydroxide, tetranonylammonium hydroxide, tetradecylammonium hydroxide, etc., of which tetramethylammonium hydroxide pentahydrate, sodium hydroxide, or potassium hydroxide is preferred, and potassium hydroxide is preferred even more.

The amount of hydroxide represented by General Formula [2] is about 0.1 mol equivalent to about 100 mol equivalent, preferably 1 mol equivalent to 20 mol equivalent against monohydroperfluoroalkane. With regards to hydroxide, when using a hydrate or an anhydrate which is assumed to adsorb water, it is preferable to remove water by drying or to add a dehydrator such as molecular sieves in the reaction system before use in a reaction, but the removal does not need to be complete. With regards to a hydrate with 5 or less hydrated water or an anhydrate, water that is included at an industrially available level, in other words, 5 wt % or less, preferably 1 wt % or less, more preferably 0.1 wt % or less against a hydroxide, is not a particular problem in carrying out the present production process, and the compound may be used without additional treatment. Hydroxides may be used as flakes, granules or powders, but powders are preferable, and a more preferable method is to use hydroxides by grinding granules before use in a reaction.

Aprotic polar solvents may be used as a solvent, and specific examples include acetonitrile, propionitrile, phenylacetonitrile, isobutyronitrile, benzonitrile, dimethylformamide, dimethylacetamide, methylformamide, formamide, N-methylpyrrolidone, N,N-dimethylimidazolidinone, hexamethylphosphoric triamide, diethyl ether, diisopropyl ether, dibutyl ether, t-butylmethyl ether, tetrahydrofuran, 1,2-dimethoxyethane, 1,3-dioxane, 1,4-dioxane, 1,2-epoxyethane, diglyme, triglyme, tetraglyme, dimethylsulfoxide, sulfolane, etc., of which dimethylsulfoxide, and sulfolane are preferable, and a combination thereof may also be used. It is also possible to combine the aforementioned aprotic polar solvents with a nonpolar solvent, such as pentane, hexane, heptane, octane, cyclohexane, benzene, toluene, xylene, ethylbenzene, etc.

The amount of solvents is about 1 to 100 weight parts, preferably 1 to 10 weight parts, against 1 weight part of a carbonyl compound represented by General Formula [1]. With regards to the solvent to be used, water may be removed before use in a reaction, or a dehydrator such as molecular sieves may be added during the reaction, but the removal of water does not need to be complete. Water that is included at an industrially available level, in other words, 5 wt % or less, preferably less than 1 wt %, more preferably 0.1 wt % or less against the solvent, is not a particular problem in carrying out the present production process, and the compound may be used without additional treatment.

After the reaction, perfluoroalkylalcohol represented by General Formula [4] may be obtained by a purification process based on a common method in organic chemistry.

EXAMPLES

The present invention is specifically explained by Examples, but the method for synthesizing a compound in the present invention is not limited by these Examples.

The compound was identified by the $^1$H nuclear magnetic resonance spectroscopy analysis (NMR), $^{19}$F NMR, and the mass spectrum analysis (GS-MS).

Example 1

[Chem. 3]

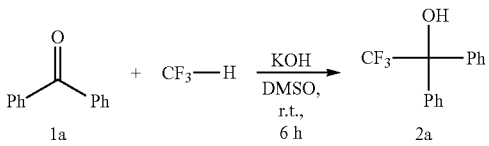

(In the formula, Ph is a phenyl group, DMSO is dimethylsulfoxide, r.t. is room temperature, 6 h is a reaction time of 6 hours.)

Under an argon atmosphere, benzophenone (1a: 1 mmol) was added to a 20 mL two-necked flask containing potassium hydroxide (1.12 g, 20 mmol, ground to a powder form in a mortar in an argon globe box) and dimethylsulfoxide (not dried, 5 mL), and then a balloon containing an excessive amount of trifluoromethane was attached. The mixture was stirred at room temperature for 6 hours, then the reaction was stopped by neutralizing the potassium hydroxide with a 4 N hydrochloric acid in an ice bath. The organic layer was extracted with diethyl ether (20 mL×3 times), washed with water (30 mL×3 times), and washed with a saturated sodium chloride aqueous solution (50 mL×1 time), then anhydrous sodium sulfate was added for drying. Sodium sulfate was removed by running the mixture through a filter, and the solvent was removed by a rotary evaporator, then a trifluoromethyl adduct 2a was obtained at a 95% yield as a white solid (on a ketone material basis).

$^1$H NMR (400 MHz, CDCl$_3$) δ: 2.86 (s, 1H), 7.35-7.37 (m, 6H), 7.48 (d, J=4.8 Hz, 4H).

$^{19}$F NMR (376 MHz, CDCl$_3$) δ: 87.5 (s, 3F).

GC-MS m/z (%): 252 (M$^+$, 10), 183 (100), 105 (94), 77 (50).

Example 2

[Chem. 4]

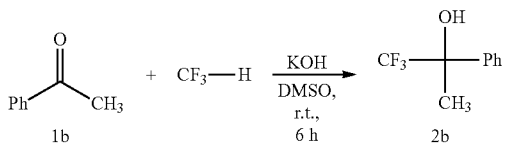

Reaction was performed under the same condition as Example 1 by changing benzophenone (1a) of Example 1 to acetophenone (1b), thereby obtaining the target product 2b as a pale yellow liquid at a yield of 84% (on a ketone material basis).

$^1$H NMR (400 MHz, CDCl$_3$) δ: 1.79 (d, J=0.8 Hz, 3H), 2.40 (s, 1H), 7.35-7.43 (m, 3H), 7.58 (d, J=7.6 Hz, 2H).

$^{19}$F NMR (376 MHz, CDCl$_3$) δ: 80.7 (s, 3F).

GC-MS m/z (%): 121 (100), 105 (33), 77 (74), 69 (22), 51 (17).

Example 3

[Chem. 5]

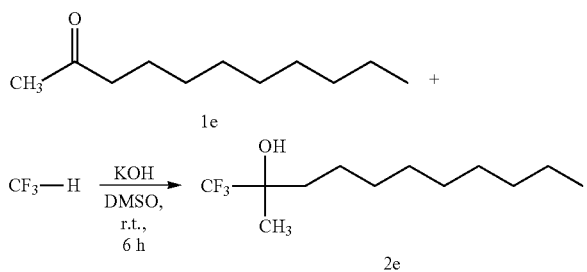

Reaction was performed under the same condition as Example 1 by changing benzophenone (1a) of Example 1 to undecan-2-one (1e), thereby obtaining the target product 2e as a colorless transparent liquid at a yield of 99% (on a ketone material basis).

$^1$H NMR (400 MHz, CDCl$_3$) δ: 0.88 (t, J=6.8 Hz, 3H), 1.27-1.31 (m, 12H), 1.34 (s, 1H), 1.38-1.49 (m, 2H), 1.62-1.67 (m, 2H), 1.81 (s, 1H).

$^{19}$F NMR (376 MHz, CDCl$_3$) δ: 78.6 (s, 3F).

GC-MS m/z (%): 171 (15), 112 (25), 97 (39), 83 (80), 70 (100), 56 (85).

Example 4

[Chem. 6]

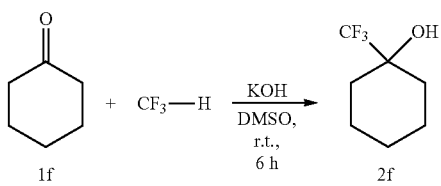

Reaction was performed under the same condition as Example 1 by changing benzophenone (1a) of Example 1 to cyclohexanone (1 f), thereby obtaining the target product 2f as a white solid at a yield of 69% (on a ketone material basis).

$^1$H NMR (400 MHz, CDCl$_3$) δ: 1.54-1.78 (m, 11H).
$^{19}$F NMR (376 MHz, CDCl$_3$) δ: 76.7 (s, 3F).
GC-MS m/z (%): 99 (100), 81 (87), 55 (30).

Example 5

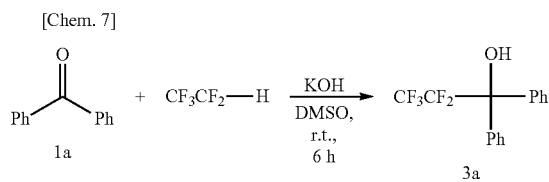

Reaction was performed under the same condition as Example 1 by changing trifluoromethane of Example 1 to pentafluoroethane, thereby obtaining the target product 3a as a colorless crystal at a yield of 43% (on a ketone material basis).

$^1$H NMR (400 MHz, CDCl$_3$) δ: 2.85 (s, 1H), 7.32-7.37 (m, 6H), 7.55 (d, J=6.8 Hz, 4H).
$^{19}$F NMR (376 MHz, CDCl$_3$) δ: 45.3 (s, 2F), 84.7 (s, 3F).
GC-MS m/z (%): 183 (63), 105 (100), 77 (53), 51 (17).

Example 6

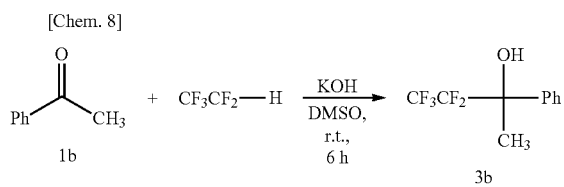

Reaction was performed under the same condition as Example 5 by changing benzophenone (1a) of Example 5 to acetophenone (1b), thereby obtaining the target product 3b as a pale yellow liquid at a yield of 56% (on a ketone material basis).

$^1$H NMR (400 MHz, CDCl$_3$) δ: 1.82 (s, 3H), 2.39 (s, 1H), 7.36-7.42 (m, 3H), 7.56 (d, J=7.6 Hz, 2H).
$^{19}$F NMR (376 MHz, CDCl$_3$) δ: 38.7 (d, J=277 Hz, 1F), 40.2 (d, J=277 Hz, 1F), 83.8 (s, 3F).
GC-MS m/z (%): 240 (M$^+$, 8), 121 (100), 86 (24), 84 (36).

Example 7

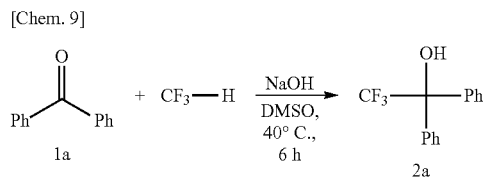

Reaction was performed under the same condition as Example 1 except for changing potassium hydroxide of Example 1 to sodium hydroxide, and changing the reaction temperature to 40° C., thereby obtaining the target product 2a at a yield of 54% (on a ketone material basis).

Example 8

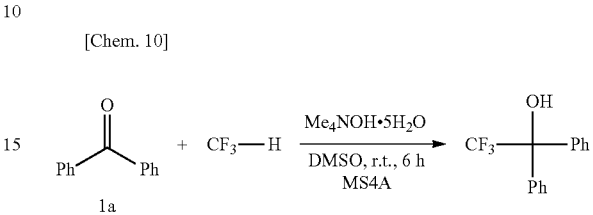

Reaction was performed under the same condition as Example 1 except for changing potassium hydroxide of Example 1 to tetramethylammonium hydroxide pentahydrate and adding molecular sieves 4 A, thereby obtaining the target product 2a at a yield of 61% (on a ketone material basis).

Example 9

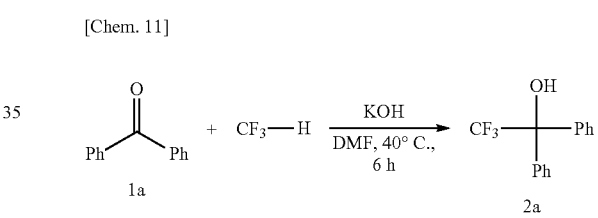

Reaction was performed under the same condition as Example 1 except for changing the solvent of Example 1 to N,N-dimethylformamide (DMF) (non-dehydrated product, 10 mL) and changing the reaction temperature to 40° C., thereby obtaining the target product 2a at a yield of 55% (on a ketone material basis).

Example 10

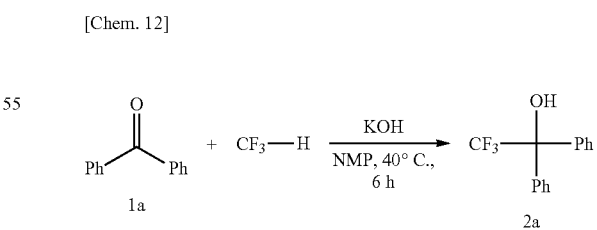

Reaction was performed under the same condition as Example 1 except for changing the solvent of Example 1 to N-methyl-pyrrolidone (NMP) (non-dehydrated product, 10 mL) and changing the reaction temperature to 40° C., thereby obtaining the target product 2a at a yield of 47% (on a ketone material basis).

Comparative Example 1

[Chem. 13]

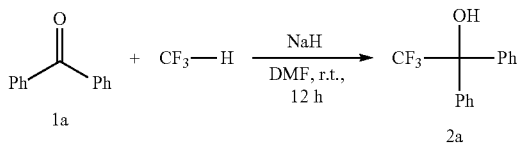

The aforementioned reaction was studied using the conditions described in Non-Patent Document 9 except for extending the reaction time from 5 hours to 12 hours, thereby obtaining the target product 2a at a yield of 62% (on a ketone material basis).

Comparative Example 2

[Chem. 14]

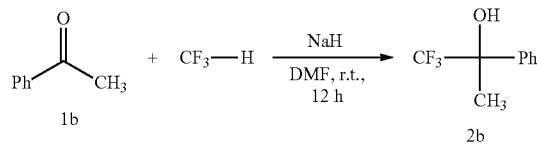

Reaction was performed under the same condition as Comparative Example 1 by changing benzophenone (1a) of Comparative Example 1 to acetophenone (1 b), thereby obtaining the target product 2b at a yield of 1% (on a ketone material basis).

Comparative Example 3

[Chem. 15]

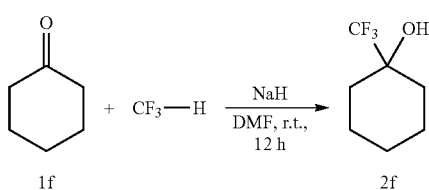

Reaction was performed under the same condition as Comparative Example 1 by changing benzophenone (1a) of Comparative Example 1 to cyclohexanone (1f), thereby obtaining the target product 2f at a yield of 6% (on a ketone material basis).

Example 11

[Chem. 16]

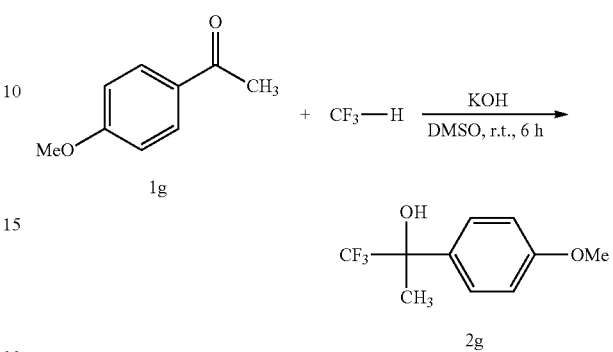

Reaction was performed under the same condition as Example 1 by changing benzophenone (1a) of Example 1 to 4'-methoxyacetophenone (1g), thereby obtaining the target product 2g at a yield of 76% (on a ketone material basis).

Example 12

[Chem. 17]

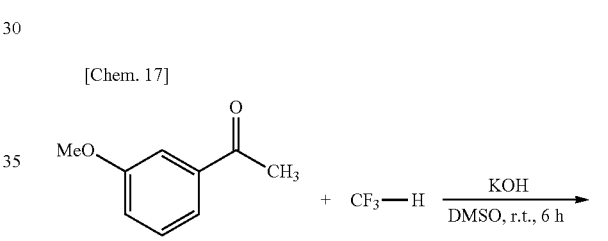

Reaction was performed under the same condition as Example 1 by changing benzophenone (1a) of Example 1 to 3'-methoxyacetophenone (1h), thereby obtaining the target product 2h at a yield of 65% (on a ketone material basis).

Example 13

[Chem. 18]

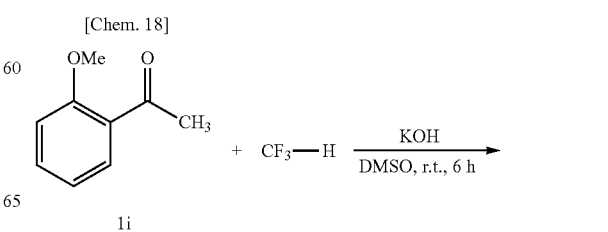

-continued

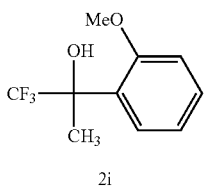

2i

Reaction was performed under the same condition as Example 1 by changing benzophenone (1a) of Example 1 to 2'-methoxyacetophenone (1i), thereby obtaining the target product 2i at a yield of 44% (on a ketone material basis).

Example 14

[Chem. 19]

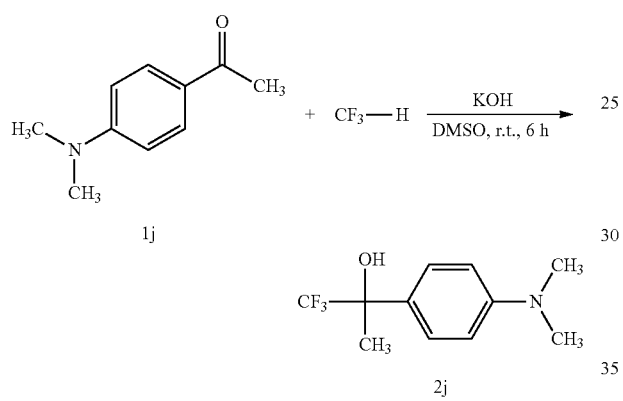

Reaction was performed under the same condition as Example 1 by changing benzophenone (1a) of Example 1 to 4'-dimethylaminoacetophenone (1j), thereby obtaining the target product 2j at a yield of 80% (on a ketone material basis).

Example 15

[Chem. 20]

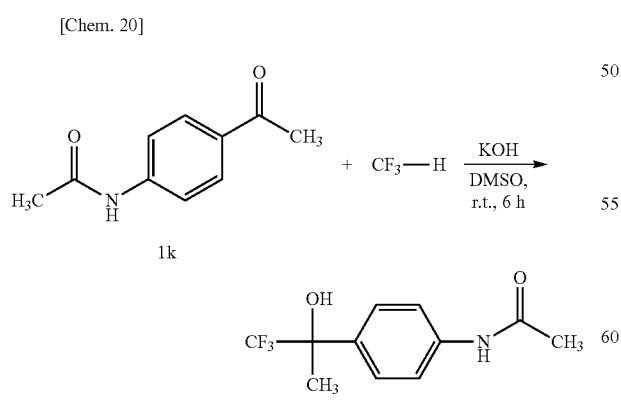

Reaction was performed under the same condition as Example 1 by changing benzophenone (1a) of Example 1 to 4'-acetamideacetophenone (1k), thereby obtaining the target product 2k at a yield of 67% (on a ketone material basis).

$^1$H NMR (400 MHz, acetone-$d_6$) δ: 1.76 (s, 3H), 2.09 (s, 3H), 5.49 (s, 1H), 7.57 (d, J=9.0 Hz, 2H), 7.67 (d, J=9.0 Hz, 2H), 9.23 (s, 1H).

$^{19}$F NMR (376 MHz, acetone-$d_6$) δ: 83.1 (s, 3F).

GC-MS m/z (%): 247 ($M^+$, 2), 178 (48), 136 (100), 120 (13), 94 (69), 77(14), 69 (5), 65 (25).

It is noted that 1-methyl-1-trifluoromethyl-1-(4'-acetamidephenyl)methyl alcohol represented by the structural formula 2k is a new compound that was first synthesized in the present invention.

Example 16

[Chem. 21]

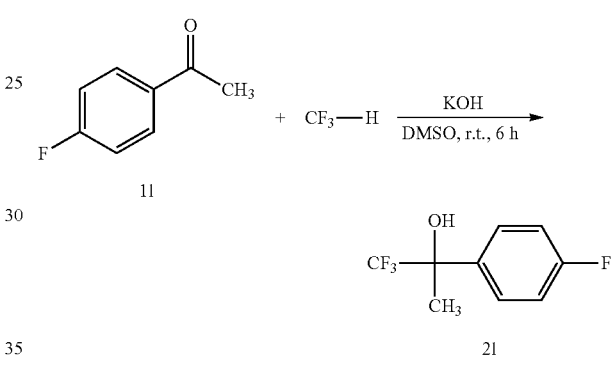

Reaction was performed under the same condition as Example 1 by changing benzophenone (1a) of Example 1 to 4'-fluoroacetophenone (1l), thereby obtaining the target product 2l at a yield of 44% (on a ketone material basis).

Example 17

[Chem. 22]

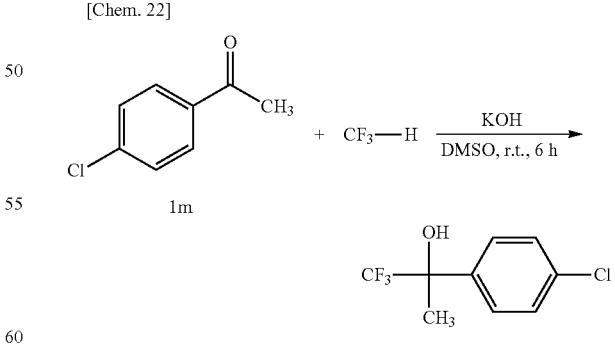

Reaction was performed under the same condition as Example 1 by changing benzophenone (1a) of Example 1 to 4'-chloroacetophenone (1m), thereby obtaining the target product 2m at a yield of 39% (on a ketone material basis).

Example 18

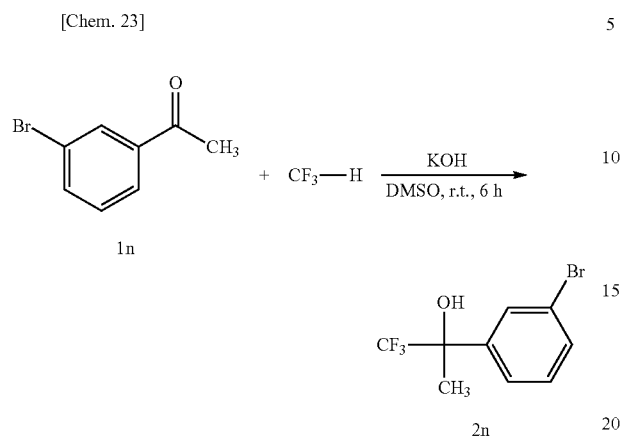

Reaction was performed under the same condition as Example 1 by changing benzophenone (1a) of Example 1 to 3'-bromoacetophenone (1n), thereby obtaining the target product 2n at a yield of 39% (on a ketone material basis).

Example 19

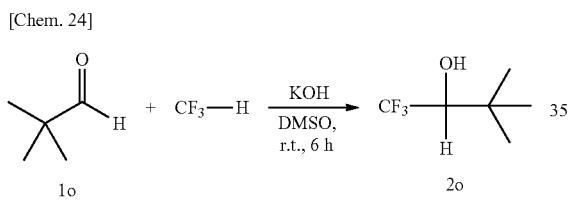

Reaction was performed under the same condition as Example 1 by changing benzophenone (1a) of Example 1 to pivalaldehyde (1o), thereby obtaining the target product 2o at a yield of 45% (on an aldehyde material basis).

The invention claimed is:

1. A production process of alcohol having a perfluoroalkyl group represented by General Formula [4]:

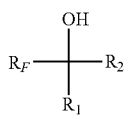

[4]

wherein, $R_F$ is a perfluoroalkyl group which is an alkyl group that may have a straight chain of 1 to 2 carbons, or a straight chain, branched chain or ring structure of 3 to 10 carbons, and which has all hydrogens on carbon substituted with fluorine; and $R^1$ and $R^2$ are each independently a hydrogen atom or an alkyl group, aryl group, heteroaryl group, aralkyl group, alkenyl group, or alkynyl group that may have a straight chain of 1 to 2 carbons, or a straight chain, branched chain or ring structure of 3 to 10 carbons, and that may have a substituent; and $R^1$ and $R^2$ may be merged to form a ring, the production process comprising: reacting in an organic solvent a carbonyl compound represented by General Formula [1]:

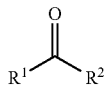

[1]

wherein $R^1$ and $R^2$ are each independently a hydrogen atom or an alkyl group, aryl group, heteroaryl group, aralkyl group, alkenyl group, or alkynyl group that may have a straight chain of 1 to 2 carbons, or a straight chain, branched chain or ring structure of 3 to 10 carbons, and that may have a substituent; and $R^1$ and $R^2$ may be merged to form a ring with monohydroperfluoroalkane represented by General Formula [3]:

 $R_FH$  [3]

wherein $R_F$ is a perfluoroalkyl group which is an alkyl group that may have a straight chain of 1 to 2 carbons, or a straight chain, branched chain or ring structure of 3 to 10 carbons, and which has all hydrogens on carbon substituted with fluorine, in the presence of a hydroxide represented by General Formula [2]:

 $M(OH)_x$  [2]

wherein, M is a metal belonging to Group I, Group II, Group III, Group IV, Group V, Group VI, Group VII, Group VIII, Group IX, Group X, Group XI, Group XII, and Group XIII in a periodic table of elements or ammonium that may be unsubstituted or that may have an alkyl group of 1 to 10 carbons as a substituent, which may be used alone or in a mixture of multiple substances, and x is equal to an oxidation number of a substance represented by M.

2. The process according to claim 1, wherein $R_FH$ represented by General Formula [3] is trifluoromethane.

3. The process according to claim 1, wherein $R_FH$ represented by General Formula [3] is pentafluoroethane.

4. The process according to claim 1, wherein $M(OH)_x$ represented by General Formula [2] is potassium hydroxide.

5. The process according to claim 1, wherein $M(OH)_x$ represented by General Formula [2] is sodium hydroxide.

6. The process according to claim 1, wherein $M(OH)_x$ represented by General Formula [2] is tetramethylammonium or a hydrate thereof.

7. The process according to claim 1, wherein $M(OH)_x$ represented by General Formula [2] is added to a reaction system as a powder.

8. The process according to claim 1, wherein the organic solvent is dimethyl sulfoxide, dimethyl formamide, N-methylpyrrolidone, tetrahydrofuran, diglyme, acetonitrile, or a combination thereof.

9. The process according to claim 1, wherein monohydroperfluoroalkane is in a gas state when it comes in contact with a reaction solution.

10. The process according to claim 1, wherein monohydroperfluoroalkane is in a liquid or solid state when it is mixed with a reaction solution.

11. The process according to claim 1, wherein the organic solvent comprises an aprotic polar solvent.

12. The process according to claim 11, wherein the aprotic polar solvent is selected from acetonitrile, propionitrile, phenylacetonitrile, isobutyronitrile, benzonitrile, dimethylformamide, dimethylacetamide, methylformamide, formamide, N-methylpyrrolidone, N,N-dimethylimidazolidinone, hexamethylphosphoric triamide, diethyl ether, diisopropyl ether, dibutyl ether, t-butylmethyl ether, tetrahydrofuran, 1,2-dimethoxyethane, 1,3-dioxane, 1,4-dioxane, 1,2-epoxyethane, diglyme, triglyme, tetraglyme, dimethylsulfoxide, sulfolane, or a combination thereof.

* * * * *